United States Patent [19]
Taylor et al.

[11] Patent Number: 5,339,822
[45] Date of Patent: Aug. 23, 1994

[54] METHOD OF VALIDATING PHYSIOLOGIC EVENTS RESULTING FROM A HEARTBEAT

[75] Inventors: Lee A. Taylor, Portland; Ronald G. Bennett, Gladstone; Herbert R. Salisbury, Beaverton, all of Oreg.

[73] Assignee: Protocol Systems, Inc., Beaverton, Oreg.

[21] Appl. No.: 72,864

[22] Filed: Jun. 4, 1993

Related U.S. Application Data

[63] Continuation of Ser. No. 696,513, May 7, 1991, abandoned.

[51] Int. Cl.$^5$ .............................................. A61B 5/04
[52] U.S. Cl. ................................................. 128/700
[58] Field of Search ............... 128/690, 696, 702, 703, 128/706, 708

[56] References Cited

U.S. PATENT DOCUMENTS

| | | | |
|---|---|---|---|
| 3,140,710 | 7/1984 | Glassner et al. | 128/700 |
| 3,707,959 | 1/1973 | Wilton-Davies | 128/703 |
| 3,734,086 | 5/1973 | Phelps, Sr. | 128/687 |
| 3,742,938 | 7/1973 | Stern | 128/687 |
| 3,807,392 | 4/1974 | Harris | 128/702 |
| 4,549,552 | 10/1985 | Groch et al. | 128/700 |
| 4,573,478 | 3/1986 | Arnold et al. | 128/687 |
| 4,869,262 | 9/1989 | Orr et al. | 128/700 |
| 4,960,126 | 10/1990 | Conlon et al. | 128/700 |
| 5,033,472 | 7/1991 | Sato et al. | 128/700 |

*Primary Examiner*—William E. Kamm
*Attorney, Agent, or Firm*—Kolisch Hartwell Dickinson McCormack & Heuser

[57] ABSTRACT

An improved method of validating pulse-like, heartbeat-induced physiologic events, such as blood-pressure pulses, is described in relation to vital signs monitoring apparatus that is also capable of monitoring R-waves obtained from an ECG sensor. The method includes the steps of monitoring the occurrence of an R-wave followed by an event of interest, and validating such event based upon analyzing, along with other preselected criteria, a time relationship extant between the R-wave and the event. The validating step includes the steps of noting the time period between selected points of the two occurrences, labeling the time period based on preselected timing criteria, and using the label with other criteria to validate the event. Events whose immediate validation is questionable are placed in a "wait and see" category for future review. The disclosed method further includes the step of repeating the monitoring, noting and labeling steps for successive R-waves and pulses, thus to establish a first measurement cycle. Also, disclosed is a step for adapting the preselected timing criteria based upon already analyzed time relationships.

6 Claims, 4 Drawing Sheets

METHOD OF VALIDATING PHYSIOLOGIC EVENTS RESULTING FROM A HEARTBEAT

This is a continuation of application Ser. No. 07/696,513 filed May 7, 1991 now abandoned.

BACKGROUND OF THE INVENTION

The present invention relates to a noninvasive method for assisting in determining parameters related to pulse-like physiologic events resulting from a heartbeat, and more particularly to a time-based method for "predetermination" validation of such events.

Examples of physiologic events resulting from a heartbeat include but are not limited to oscillometric pulses, K-sounds, invasive arterial blood-pressure pulses, tonometric non-invasive arterial blood-pressure pulses, plethysmographic pulses due to absorption of infrared and near-infrared light by a living subject's blood, heart sounds, cardiogenic oscillations in thoracic impedance waveforms, cardiogenic oscillations in capnograms, and pulsatile components of the airway pressure waveform. With each such event, there is a clearly detectable pulse-like activity with respect to which predetermined points may be selected for reliable time-relationship examination in accordance with the teachings of the present invention.

To illustrate the present invention, a description thereof will be given in the context of validating oscillometric pulses, with the understanding that the invention may be practiced in connection with heartbeat-related physiologic events such as those mentioned above.

Regarding oscillometry, it is known to measure blood pressure noninvasively by monitoring and analyzing pressure pulsations occurring in a blood-vessel-occluding cuff that has been inflated to a supra-systolic pressure and then gradually deflated in steps to below diastolic pressure.

To provide an accurate method of determining blood pressure, there is a need for addressing the problem of artifact, i.e. non-blood-pressure-induced, pulse-like information. Regardless of what is causing such artifact, it is important to provide a method of determining when pulse-like, or pulsatile, information is true (i.e. blood-pressure induced) and when it is false (i.e. non-blood-pressure induced) so that corresponding monitoring apparatus can be smart enough to recognize the difference and discard the false data.

In circumstances where unmistakenably "true" pulse information is not clearly available, it is important also that the method of the invention accept, alternatively, promising "borderline" information.

Similar artifact issues are involved with other heartbeat-resultant physiologic events.

Various conventional methods have been proposed to deal with the problem of artifact. Such methods include the use of a monitored time relationship between an R-wave from an ECG sensor and an oscillometric pulse from a blood-pressure monitor.

For example, in U.S. Pat. No. 4,974,597 there is disclosed a method of verifying an oscillometric pulse by checking whether a single pulse is detected between successive QRS complexes sensed by an ECG monitor.

U.S. Pat. No. 4,216,779 illustrates a Korotkov-based blood-pressure monitoring system that accepts, preliminarily, a first K-sound if it is detected within a predetermined time period after a heartbeat is detected. Then, the first K-sound is accepted ultimately if a second, later K-sound is detected within the time period.

Other such methods are disclosed in U.S. Pat. Nos. 4,349,034 to Ramsey, III, 4,889,133 to Nelson et al. and 4,949,710 to Dorsett et al., which focus on artifact rejection based on criteria such as pulse slope, pulse period, pulse amplitude, pulse area and pulse-area prediction. These criteria are referred to herein as other preselected criteria. It should be understood that other criteria as used herein may include any conventional criteria, including but not limited to those listed above.

An important object of the present invention is to deal with the above-identified problem by providing an improved method of validating heartbeat-induced physiologic events, such as pulsatile blood-pressure information.

A further object of the invention is to provide a way of validating such information by analyzing, along with other preselected criteria, a time-interval relationship extant between pairs of oscillometric pulses and R-waves.

SUMMARY OF THE INVENTION

The present invention, as illustrated below, accomplishes the above objects by providing an improved method of validating oscillometric pulses of blood-pressure information monitored by vital signs monitoring apparatus that is also capable of monitoring R-waves obtained from an ECG sensor. The method includes the steps of monitoring the occurrence of an R-wave and such a pulse within a defined range of available blood-pressure information, and validating such pulse based upon analyzing, along with other preselected criteria, a time relationship extant between the R-wave and the individual pulse.

The validating step includes the steps of noting the time period between selected points of the two occurrences, labeling the time period based on preselected timing criteria, and using the label with other criteria to validate the pulse.

The method of the invention further includes the step of repeating the monitoring, noting, labeling and using steps for successive R-waves and pulses that occur within the defined time range, thus to establish a first measurement cycle. Also involved, according to the current preferred manner of practicing the invention, is adapting the preselected timing criteria for a later measurement cycle based upon the time relationships analyzed in earlier measurement cycles. One could of course, if desired, conduct analysis and adaptation within a given cycle.

These and additional objects and advantages of the present invention will be more readily understood after a consideration of the drawings and the detailed description of the preferred manner of practicing the invention.

DETAILED DESCRIPTION OF THE PREFERRED MANNER OF PRACTICING THE INVENTION

Before turning to the drawings, it is important to understand that the invention is focused on validating pulsatile (pulse-like) physiologic events, such as oscillometric pulses carrying blood-pressure information. The to-be-described steps of the invention may be practiced by writing them into computer programs that may be stored in the memory of control/processing circuitry of otherwise conventional vital signs monitoring apparatus.

As was mentioned above, the following description will relate to monitoring and validating blood-pressure information in the form of oscillometric pulses, with the understanding that various other kinds of heartbeat-induced physiologic events can be handled in the practice of the invention.

Figure 1:
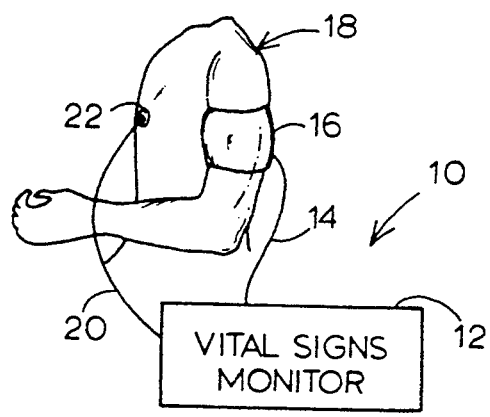
FIG. 1 is a partial view of a living subject having certain vital signs being monitored with vital signs monitoring apparatus (shown in schematic block diagram) suitable for practicing the method of the present invention.

Referring now to FIG. 1, conventional vital signs monitoring apparatus is shown at 10 with a monitor 12 and a conduit 14 coupled to an occluding cuff 16 that is fitted around an arm of a living subject 18. A conductive cable structure 20 interconnects monitor 12 with an ECG lead 22. Any conventional ECG-lead arrangement may be used.

Continuing with FIG. 1, monitor 12 is a microprocessor-controlled device that includes the usual pump, (for cuff 16, and not shown herein) and sensors/transducers (for cuff 16 and ECG lead 22, also not shown herein). Apparatus 10 also includes the usual integrated circuitry for controlling the monitor, for converting analog-signal-data (fed from cuff 16 and lead 22) to digital-signal-data, and for processing the digital-signal-data to determine vital signs parameters. As known to those skilled in the art, such circuitry includes a microprocessor, RAM for acquiring data, and ROM for storing computer programs that direct the microprocessor to control the monitor and to process data.

As is known to those skilled in the art, apparatus 10 is usable to measure a subject's blood pressure and heart rate during a suitable measurement cycle. For practicing the present invention, the usual NIBP-cycle may be used as a measurement cycle in the practice of the present invention. Such cycle includes monitoring and processing pressure-signal information from cuff 16 for a defined range of pulsatile information, i.e. from a suprasystolic pressure (cuff inflated) to below diastolic pressure (cuff step-wise deflated).

During a measurement cycle, conduit 14 will convey analog-signal-data in what may be thought of as a stream of pulsatile information and cable structure 20 will convey what may be thought of as a stream of QRS complexes. Such stream of QRS complexes will be referred to herein as an R-wave stream. For a detailed description of a NIBP-cycle, one may look to U.S. Pat. No. 4,889,133 to Nelson et al., which patent is incorporated herein by reference.

Figure 2:
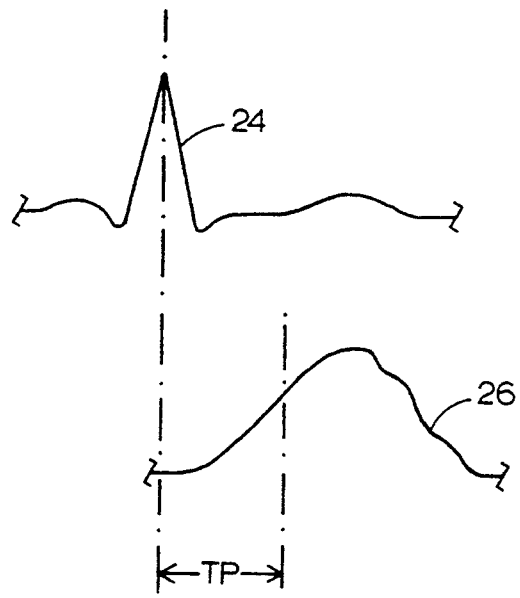
FIG. 2 shows, on a common horizontal time base, a monitored time relationship TP between an R-wave and an oscillometric pulse (heartbeat-related physiologic event) during a measurement cycle practiced according to the invention.

Before describing the computer programs for carrying out the steps of the invention, FIG. 2 will be described to illustrate generally applicants' novel way of noting and labeling time periods between R-waves and pulses. FIG. 2 shows (top of the figure) a fragmentary portion of an R-wave stream from cable structure 20 and (bottom of the figure) a portion of a pulsatile-information stream from conduit 14. An R-wave is indicated at 24, and a unit of pulsatile information (pulse) is shown at 26. Preferably, and in the specific illustration now being given, TP is the monitored time period between the occurrence (peak) of R-wave 24 and a selected point on pulse 26, which point herein is chosen to coincide with that where the first derivative of the pulse reaches a maximum absolute value. Those skilled in the art will recognize that there are numerous points between which one could choose to determine TP.

Figure 3:
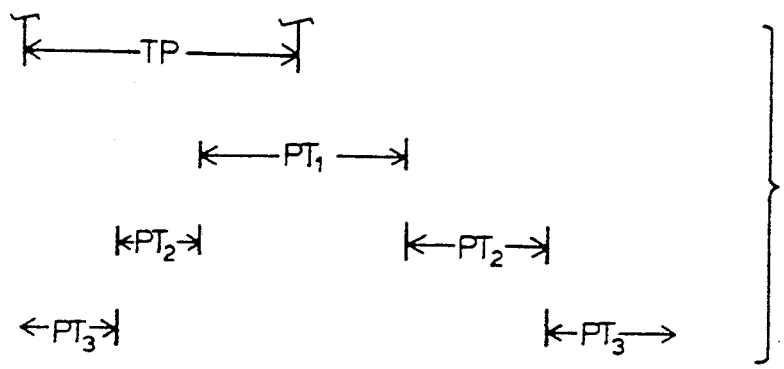
FIG. 3 augments (on an enlarged scale) FIG. 2 by showing preselected timing criteria that relate to the TP time relationship.

Referring now to FIG. 3, $PT_1$ is the label applicants have experimentally determined to be a normal time range for such a time period in adults. Those skilled in the art will know immediately how to set up similar periods for pediatric and neonatal patients. $PT_2$ and $PT_3$ are labels given to related, experimentally determined normal-adult borderline ranges and abnormal ranges, respectively.

To practice the method of the present invention, $PT_1$–$PT_3$ are:

| Label | Range/msec |
| --- | --- |
| Normal ($PT_1$) | 110–275 |
| Borderline ($PT_2$) | 82.5–110, 275–385 |
| Abnormal ($PT_3$) | <82.5 or >385 |

Applicants have found that by noting such time periods between pairs of individual R-waves and individual pulses, and labeling the same based upon the above preselected timing criteria, the labeled time periods can be used with other criteria to validate pulses. As was mentioned earlier, such other criteria may be any or all of the criteria referred to above in the background section.

Also before describing the computer programs for carrying out the steps of the invention, the validating step will be described generally. As stated above, the invention embodiment now being described proposes validating a pulse of blood-pressure information (e.g. pulse 26 of FIG. 2) based upon analyzing, along with other preselected criteria, a time relationship (TP) extant between an R-wave and the pulse (e.g. R-wave 24 and pulse 26).

The following example is provided to illustrate generally what is meant by validating the pulse "based upon analyzing, along with other criteria . . . ". The example will show how the validating step may be practiced in connection with pulse 26 of FIG. 2. A single other criterium will be used, i.e. the pulse-prediction criterium disclosed in U.S. Pat. No. 4,949,710 to Dorsett et al. It should be understood that the choice of which other criterium or combination of criteria is not critical. Rather, the described practice of the invention is focused on providing an improved method of validating a pulse of blood-pressure information (in this example—pulse 26) based upon analyzing TP with other criteria, whichever other criteria those skilled in the art may choose.

For the example, say that TP for pulse 26 is 150-msec. As will be described further in connection with FIGS. 4–7, monitor 12 will note TP and label it as normal because it is within $PT_1$ (FIG. 3), the normal range based upon the preselected timing criteria shown above.

For pulse 26, say that monitor 12 (FIG. 1) predicted that it would have an area-data value of AP according to the pulse-area-prediction method disclosed in U.S. Pat. No. 4,949,710, which patent is incorporated herein by reference. Further, say that pulse 26 has a monitored area-data value of 0.75AP. To evaluate the other criteria (criterium in this example) according to a to-be-described Pulse-Validator Program (FIG. 6), monitor 12 is directed to access the monitored area-data value from RAM and label to it as normal, borderline or abnormal based upon the following preselected ranges:

| Label | Range |
| --- | --- |
| Normal | .7AP–1.3AP |
| Borderline | .4AP–.7AP, 1.3AP–2.6AP |
| Abnormal | <.4AP, >2.6AP |

Monitor 12 will label pulse 26 as normal according to the other criterium because the monitored area-data value 0.75AP is within the above-identified normal range. The decision for establishing the exact ranges for when the other criteria are normal, abnormal or borderline is capable of being made by those skilled in the art. To practice the invention, it is important to know that such an accessing/labeling step is done when analyzing TP with other criteria.

Figure 6:
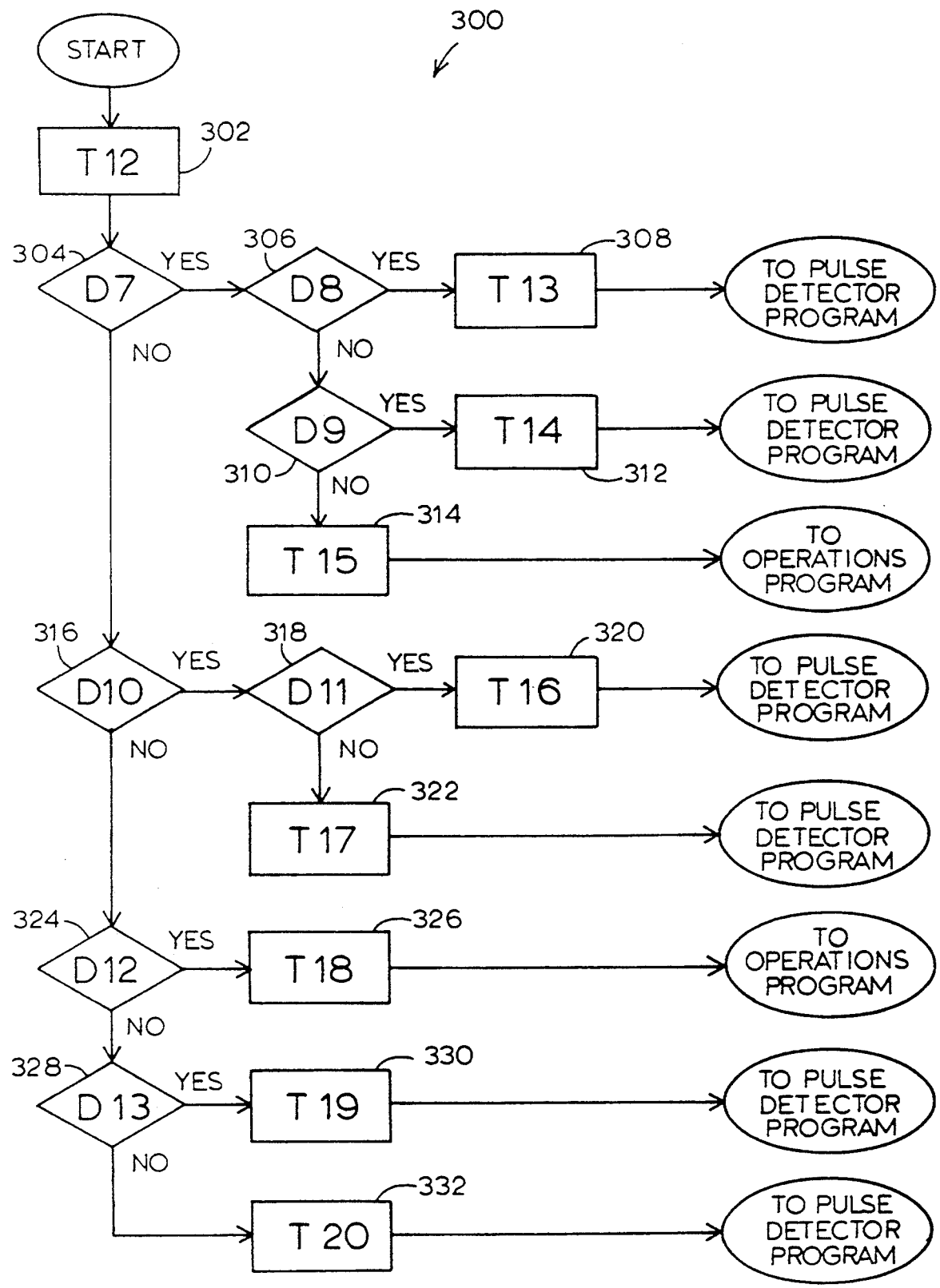
FIG. 6 shows a flow diagram of the logical steps for practicing the labeling and using steps of the invention.

Next, monitor 12 will use the other criterium with the TP for pulse 26 by following to-be-described decisions and tasks shown in FIG. 6 (Pulse-Validator Program 300). According to the TP and pulse-prediction criterium above, monitor 12 will validate pulse 26 because TP is normal and the other criterium is normal.

As those skilled in the art will recognize, if monitor 12 uses more than two other criteria, and if monitor 12 uses preselected normal, borderline, and abnormal ranges for TP, majority of other criteria ("MOC"), and all other criteria ("AOC"), the following twelve outcomes (Chart I below) are possible for validating a pulse based upon analyzing TP with other criteria:

CHART I

| Other Criteria | TP Normal | TP Borderline | TP Abnormal |
| --- | --- | --- | --- |
| AOC normal | accept | accept | WAS ("Wait and see") |
| MOC normal | accept | WAS | reject |
| MOC borderline | WAS | reject | reject |
| MOC abnormal | reject | reject | reject |

One other outcome should be discussed. This relates to a case where, strictly speaking, the reviewed other criteria do not display a true majority. In this case, we treat this result as an "MOC borderline" case, with the same handling depicted in the table immediately above.

In the implementation of the invention as presented herein, time periods are characterized in terms of "normal", "borderline" and "abnormal". These three categories have been found to offer a high degree of utility in practicing the invention, but one skilled in the art should recognize that such categories are merely reflective of the somewhat broader concept that there is a range of time-period characteristics which stretches from one wherein acquired pulses are readily and immediately verifiable as "true" pulses to an opposite extreme wherein acquired pulses are readily and immediately verifiable as "false" pulses. There are also acquired pulses which may be verifiable as "true" pulses. With respect to the latter category of pulses, a feature of the present invention is the selected labeling of such possibly verifiable pulses' respective "time periods" as wait-and-see pulses. The notion, of course, here, is that if during a monitoring operation no "better" pulses, i.e. readily and immediately verifiably "true" pulses, are found, one may elect to accept as valid the so-called wait-and-see pulses.

Referring to the above table, WAS refers to a "wait and see" approach that is practiced as part of the validating step. As will be described in connection with FIG. 6, the present invention practices the validating step and analyzes the above outcomes via Pulse-Validator Program 300. When monitor 12 recognizes that one of the above WAS outcomes has occurred, program 300 will direct it to save the present pulse as a provisional pulse. If no better pulse is monitored and analyzed (at the same cuff-pressure step) within a subsequent 5-second interval, then another program, Pulse-Detector Program 200 (FIG. 5), will direct monitor 12 to save, and thus validate, the pulse (and a conventional operations program will direct the monitor to decrease cuff pressure in a step-wise manner).

FIGS. 4–7 show flow charts from which suitable software can readily be written by those skilled in the art to practice the steps of the invention. The programs may start through an operator command, automatically at power-up or when called by another program stored in ROM. The usual initializing step is carried out to set up the software for subsequent processing.

Figure 4:
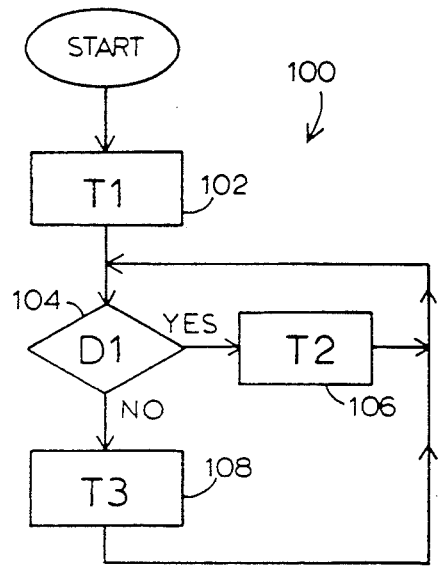
FIG. 4 shows a flow diagram that relates to the monitoring step showing the logical steps for an R-wave timing program usable with the apparatus of FIG. 1.

The following table is a reference for the immediately following description of FIG. 4:

TABLE I

| TIMING PROGRAM | |
| --- | --- |
| (D1) | Has an R-wave been detected? |
| (T1) | Initialize Time Since R-Wave to Zero |
| (T2) | Reset Time Since R-Wave to Zero |
| (T3) | Increment Counter of Time Since Last R-Wave |

Turning to FIG. 4, a flow diagram of a timer program 100 is shown that directs the microprocessor to track continuously the time since a last R-wave has been monitored. First, task block 102 (T1) initializes the time since an R-wave has been detected to zero. Such step is performed within monitor 12 (FIG. 1) at the start of a to-be-described measurement cycle. Then, decision block 104 (D1) asks whether monitor 12 has detected an R-wave. If the answer is yes, then the program proceeds to task block 106 (T2) where the time since detecting the last R-wave is reset to zero. From task block 106 (T2) the program loops back to decision block 104 (D1).

If the answer to decision block 104 (D1) is no, then the program goes to task block 108 (T3) where a data, or sample, counter is advanced by one increment. From task block 108 (T3) the program loops back through to decision block 104 (D1).

Figure 5:
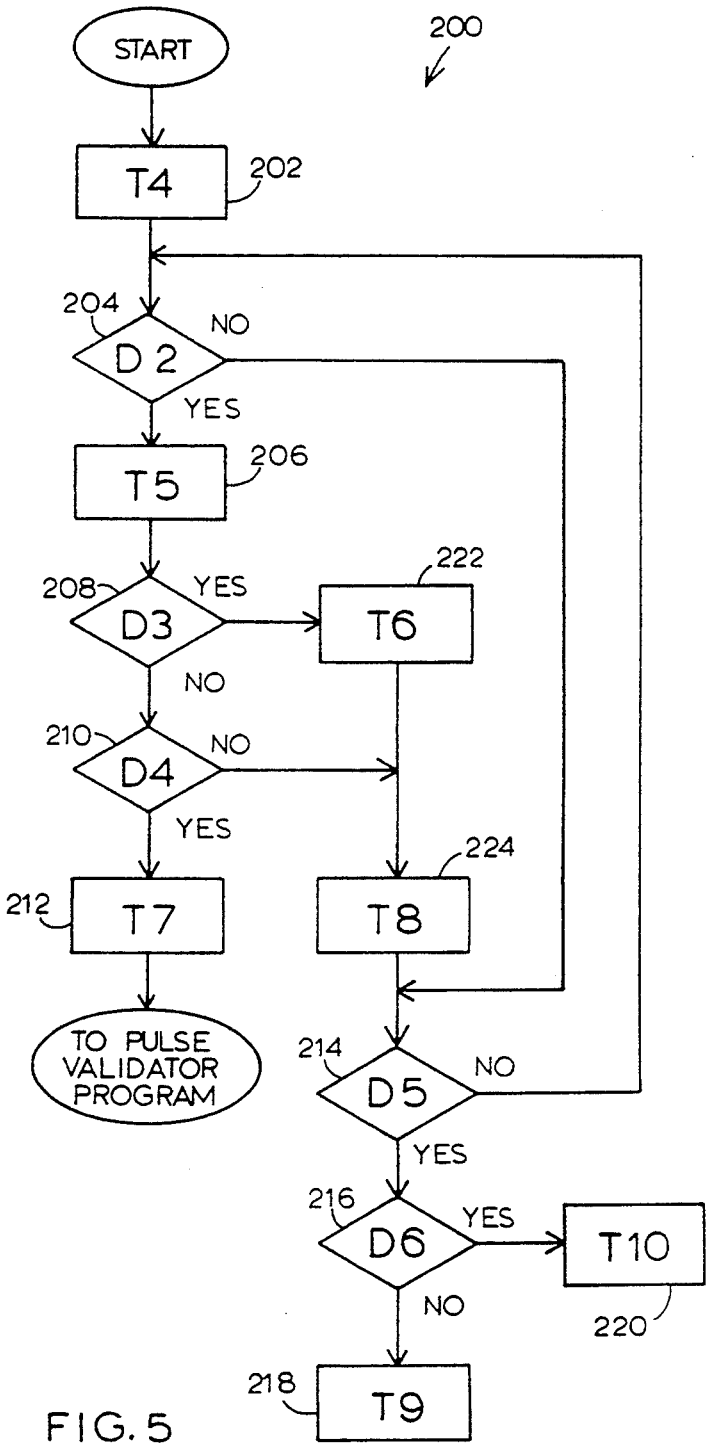
FIG. 5 shows a flow diagram of the logical steps for practicing the noting step of the invention.

Before describing FIGS. 5–6, a few comments are required. As noted above, FIGS. 5–6 depict logical steps for performing the noting, labeling and using steps of the invention. A pulse is validated as a result of practicing these steps. It should be understood that when the phrase "accept the pulse" or "accept the provisional pulse" is used herein, it means that the microprocessor is directed to save the data sample corresponding to that pulse, and to use it in desired conventional determination of blood-pressure parameters. When the phrase "reject the pulse" is used herein, it means that microprocessor is directed to reject the data sample corresponding to that pulse and thus disregard it.

The following table is a reference for the immediately following description of FIG. 5:

TABLE II

| Pulse-detector PROGRAM | |
|---|---|
| (D2) | Is Gradient ≧ Start Threshold and Previous Gradient < Start Threshold? |
| (D3) | Is Gradient > Max Gradient Found? |
| (D4) | Is Gradient < Zero? |
| (D5) | Have 5-Seconds Elapsed? |
| (D6) | Was a Provisional Pulse Saved? |
| (T4) | Initialize Maximum Gradient Found to Zero |
| (T5) | Start of Pulse Detected |
| (T6) | Label Gradient as Max Gradient Found - Note Time Period (TP) as Time Since Last R-Wave |
| (T7) | Possible Pulse Detected; Evaluate Pulse in Block 3 |
| (T8) | Wait for Next Sample |
| (T9) | No Acceptable Pulse Found |
| (T10) | Accept Provisional Pulse |

Referring to FIG. 5, pulse-detector program 200 includes task block 202 (T4) which initializes a present maximum gradient to zero. Next, the program proceeds to decision block 204 (D2) where it asks whether the gradient is ≧ a preset threshold and whether the immediately previous gradient was < the preset start threshold.

If the answer to block 204 (D2) is yes, then the program proceeds to task block 206 (T5) and tells the microprocessor that the start of a pulse is being detected. From block 206 (T5), the program proceeds to decision block 208 (D3) where it asks whether the gradient is greater than the maximum gradient found. If the answer is no, the program goes to decision block 210 (D4) where it asks whether the gradient is < zero. If the answer is yes, the program proceeds to task block 212 (T7) where it reports that a possible pulse is being detected and exits to pulse-validator program 300 which will be described below in connection with FIG. 6.

If the answer to block 204 (D2) is no, the program proceeds to decision block 214 (D5) which asks whether a number of counts corresponding to 5-seconds have been incremented by timing program 100. If the answer to block 214 (D5) is no, the program then loops back to decision block 204 (D2) and the above steps are repeated for a next data sample. If the answer to block 214 is yes, the program proceeds to decision block 216 (D6) where it asks whether a provisional pulse has been saved.

At block 216 (D6), if the answer is no, the program proceeds to task block 218 (T9) where it reports that no acceptable pulse has been found. If the answer is yes, the program proceeds to task block 220 (T10) where it reports that the provisional pulse should be accepted and saved.

Referring back to the yes-answer possibility of block 208 (D3), the program goes to task block 222 (T6) where the present gradient is labeled the maximum gradient, and TP is noted as the time (in counter increments) since the last R-wave was detected. As stated above, such time is monitored continuously via timing program 100 (FIG. 4). From task block 222 (T6), the program proceeds to task block 224 (T8) where it is told to wait for a next data sample, and is routed to block 214 (D5) where it will follow the above-described steps.

Referring back to the no-answer possibility of block 210 (D4), the program proceeds to task block 224 (T8) where it is performs the tasks and makes the decisions described above.

The following table is a reference for the immediately following description of FIG. 6:

TABLE III

| Pulse-validator PROGRAM | |
|---|---|
| (D7) | Is TP Normal? |
| (D8) | Is Majority of Other Criteria ("MOC") Abnormal? |
| (D9) | Is MOC Borderline? |
| (D10) | Is TP Abnormal? |
| (D11) | Are All Other Criteria ("AOC") Normal? |
| (D12) | Are AOC Normal? |
| (D13) | Are MOC Normal? |
| (T12) | Access Other Criteria From RAM and Determine if MOC and AOC are Normal, Borderline or Abnormal |
| (T13) | Reject Pulse |
| (T14) | Save Pulse as Provisional Pulse |
| (T15) | Accept and Save Pulse |
| (T16) | Save Pulse as Provisional Pulse |
| (T17) | Reject Pulse |
| (T18) | Accept and Save Pulse |
| (T19) | Save Pulse as Provisional Pulse |
| (T20) | Reject Pulse |

Turning to FIG. 6, a pulse-validator program 300 is shown. Preliminarily, it should be understood that examples of the labeling step of the invention are shown at to-be-described decision blocks D7 and D12, and examples of the using step are shown at D8, D9, and D11–D13.

Continuing with FIG. 6, program 300 starts at task block 302 (T12) where it directs the microprocessor to access other criteria from RAM. Such criteria may be any known pulse-evaluation criteria, including but not limited to those described above. As will be described below, and for a given pulse, program 300 groups the other criteria as "majority of other criteria" ("MOC") and "all other criteria" ("AOC"), and then uses information relative to the MOC and AOC with TP to validate the pulse. Program 300 obtains such information by checking RAM which contains for each monitored pulse other monitored criteria such as the pulse-area-prediction criterium discussed above in connection with FIG. 3.

Still referring to task block 302 (T12), the program determines whether the MOC and AOC are in a preselected normal, borderline or abnormal range. An example of such preselected ranges are those shown in FIG. 3 that correspond to the corresponding ranges for the time relationship extant between the R-wave and the pulse. Another example of such ranges was provided above in connection with the pulse-area-prediction criterium discussed in an example after the description of FIG. 3. Those skilled in the art will know how to establish such ranges for other criteria.

Still referring to FIG. 6, the program goes from block 302 (T12) to decision block 304 (D7) where it asks whether the time period (TP) is normal. If the answer is yes, the program proceeds to decision block 306 (D8) where it asks whether MOC are abnormal. If the answer is yes, then the program proceeds to task block 308 (T13) where it directs the microprocessor to reject the pulse, exit program 300 and go to program 200 to detect and evaluate more data samples.

If the answer to decision block 306 (D8) is no, the program goes to decision block 310 (D9) where it asks whether the MOC are borderline. If the answer is yes, the program proceeds to task block 312 (T14) where it saves the pulse as a provisional pulse, exits program 300 and goes to program 200 to perform pulse detection and evaluation.

If the answer to block 310 (D9) is no, the program goes to task block 314 (T15) where it accepts and saves the pulse and exits to a suitable operations program (undepicted).

Referring back to the possibility of a negative answer to decision block 304 (D7), the program goes to decision block 316 (D10) where it asks whether the TP is abnormal. If the answer is yes, the program proceeds to decision block 318 (D11) where it asks whether all criteria are normal. If the answer to block 318 (D11) is yes, the program proceeds to task block 320 (T16) where it saves the pulse as a provisional pulse, exits program 300 and goes to program 200.

If the answer to decision block 318 (D11) is no, the program goes to task block 322 (T17) where it rejects the pulse, exits program 300 and goes to program 200.

Referring back to the possibility of a negative answer to decision block 316 (D10), the program goes to decision block 324 (D12) where it asks whether all criteria are normal. If the answer to block 324 (D12) is yes, the program proceeds to task block 326 (T18) where it accepts and saves the pulse and exits to a suitable operations program (undepicted).

If the answer to decision block 324 (D12) is no, the program proceeds to decision block 328 (D13) where it asks whether the MOC are normal. If the answer is yes, the program proceeds to task block 330 (T19) where it saves the pulse as a provisional pulse, exits program 300 and goes to program 200. If the answer to decision block 328 (D13) is no, the program goes to task block 332 (T20) where it rejects the pulse, exits program 300 and goes to program 200.

Figure 7:
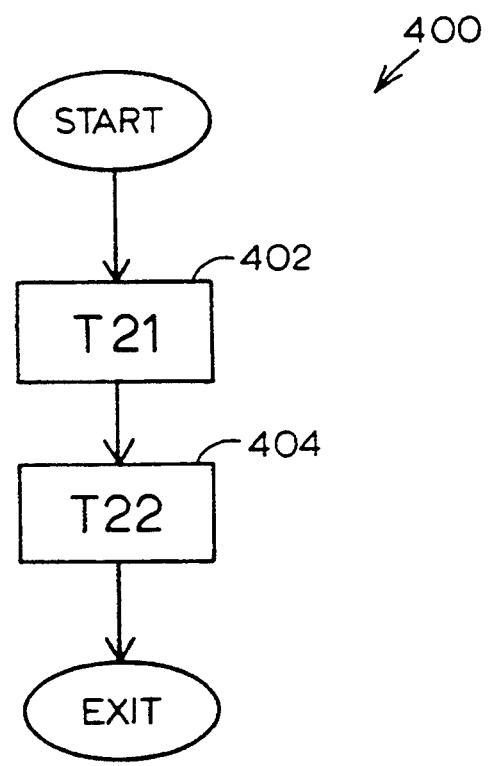
FIG. 7 shows a flow diagram of the logical steps for practicing the adapting steps of the invention.
Figure 4:
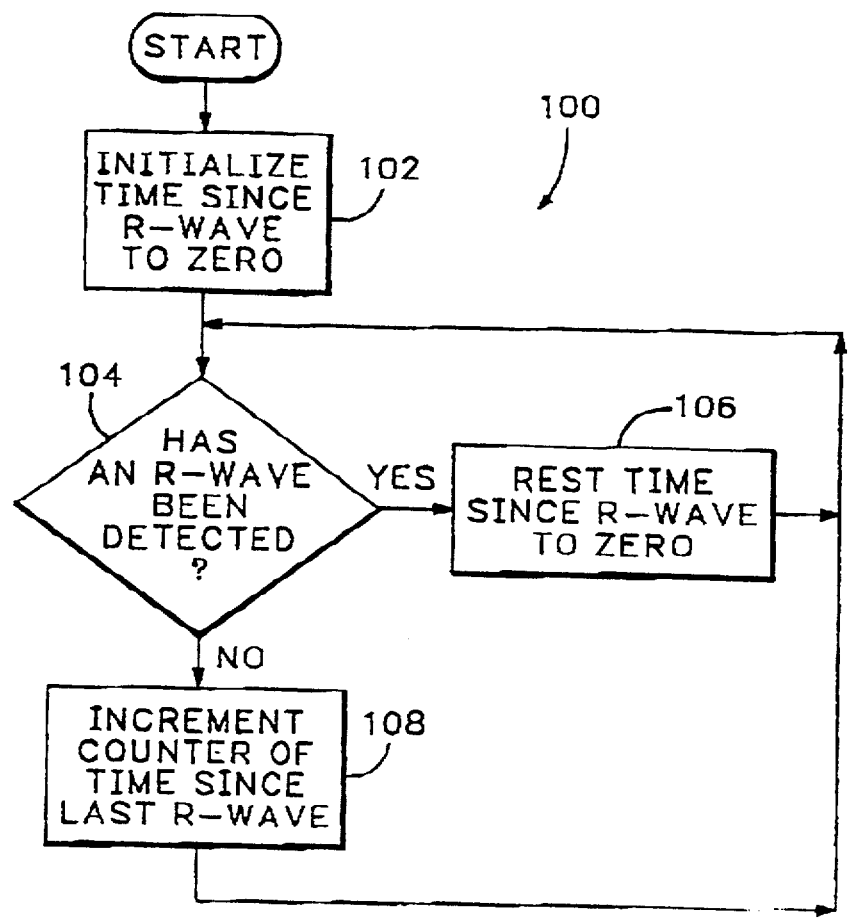
Figure 5:
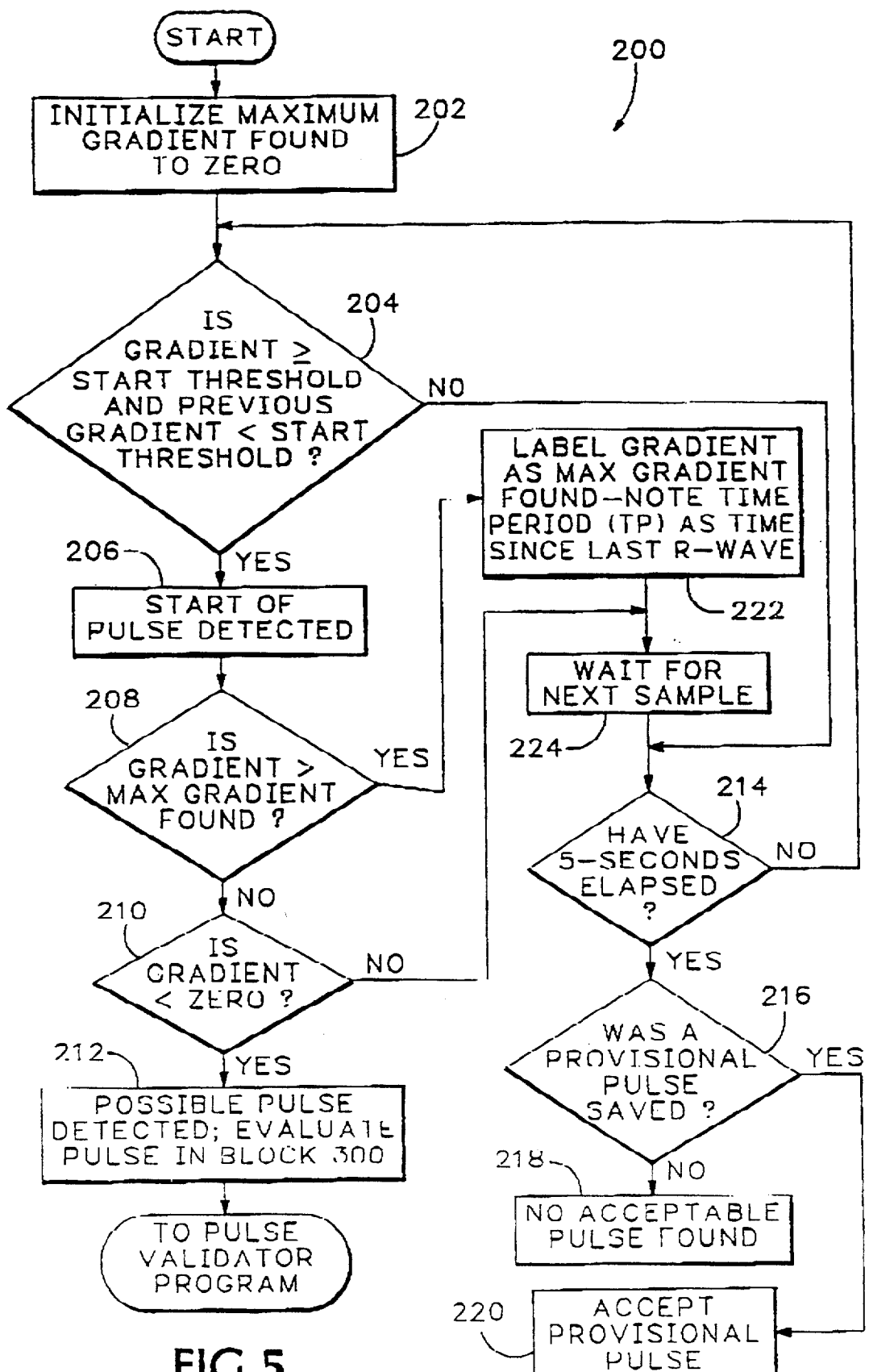
Figure 6B:
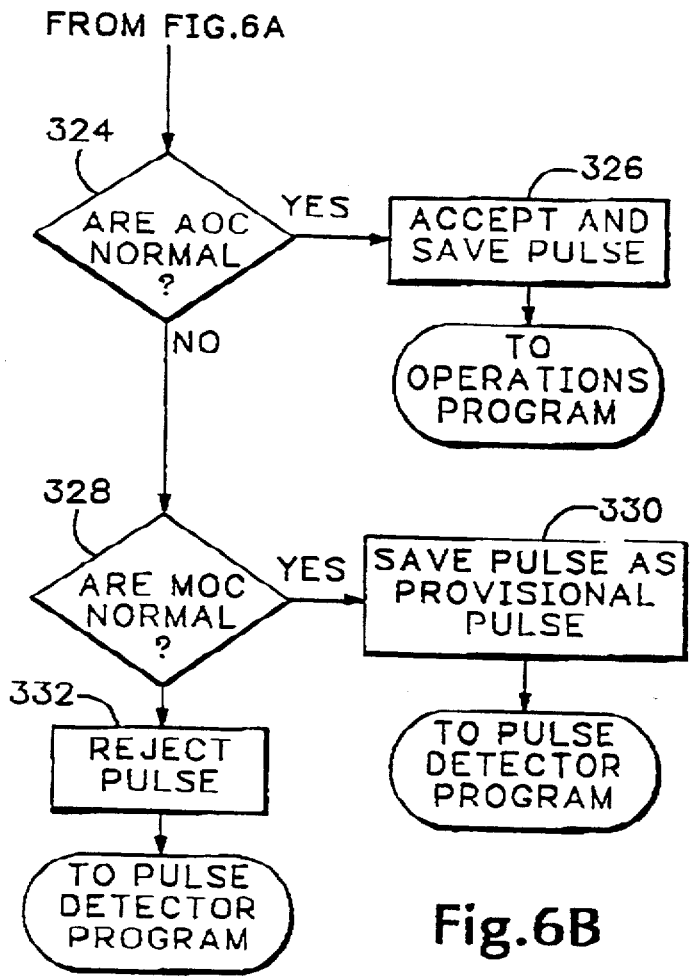
Figure 7:
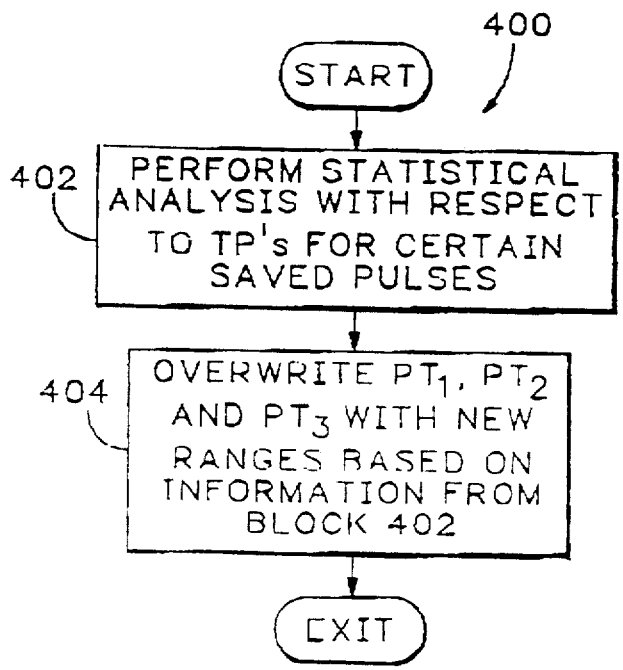

The following table relates to the immediately following description of FIG. 7:

TABLE IV

| | ADAPTOR PROGRAM |
|---|---|
| (T21) | Perform Statistical Analysis With Respect to TP's for Certain Saved Pulses |
| (T22) | Overwrite $PT_1$, $PT_2$ and $PT_3$ With New Ranges Based on Information from T21. |

Referring to FIG. 7, apparatus 10 also includes an adaptor program 400 for adapting the preselected timing criteria shown in FIG. 3 based upon time relationships between R-waves and pulses already analyzed. While such analyzing, and resulting adaptation, can occur if desired as speedily as within a given measurement cycle, we have found it currently convenient and entirely satisfactory to perform these steps based upon earlier, completed measurement cycles. Accordingly, after a measurement cycle has been performed in monitor 12 (FIG. 1), an operations program (undepicted) goes to adaptor program 400. At task block 402 (T21), the program performs a statistical analysis with respect to TP's for certain previously detected and saved pulses, and determines a mean TP and a standard deviation from such analysis. Presently, the saved pulses that are used at block 402 (T21) are those corresponding to validated pulses with TP's normal and AOC normal, with TP's normal and MOC normal or borderline, with TP's borderline and AOC or MOC normal, and with TP's abnormal and AOC normal.

For the possible situation where there are no validated pulses available, it is presently contemplated to use certain pulses that are the best available. In other words, for the latter situation, pulses with abnormal TP and MOC borderline or pulses with TP borderline and MOC borderline would be saved for use at block 402 (T21).

Still referring to FIG. 7, the program proceeds to task block 404 (T22) where it adapts the timing criteria shown in FIG. 3 by overwriting $PT_1$, $PT_2$ and $PT_3$. The new timing criteria are written into memory as follows:

| Label | Range/msec |
|---|---|
| Normal ($PT_1$) | mean TP ± 2-standard deviations |
| Borderline ($PT_2$) | between ±2- and ±3-standard deviations from mean TP |
| Abnormal ($PT_3$) | > ±3-standard deviations from mean TP |

The above-proposed set of ranges is but one of many that those skilled in the art might wish to choose for verification purposes.

SUMMARY

From the above description of programs 100–400 (FIGS. 4–7), the method of the invention should now be apparent. To summarize: the monitoring step of the invention is carried out via programs 100 and 200; the validating step via program 300; and the adapting step via program 400. Programs 200 and 300 are also usable to carry out the repeating step, designed as they are to exit to each other, thus allowing the monitoring and validating steps to be repeated for successive pairs of individual R-waves and pulses within the a first measurement cycle.

This unique organization offers a highly reliable, and hence successful, method for validating heartbeat-induced, pulse-like, physiologic events. An interesting potential of the method of the present invention is that heart-induced pulsatile events of interest may be validated even in certain arrhythmia situations. Such is made realizable because of the proposed validation focus which interlaces and relates R-wave/event time relationships with other credible criteria.

While the present invention has been shown and described with reference to the foregoing preferred manner of practicing it, those skilled in the art will understand that other changes in form and detail may be made therein without departing from the spirit and scope of the invention as defined in the appended claims.

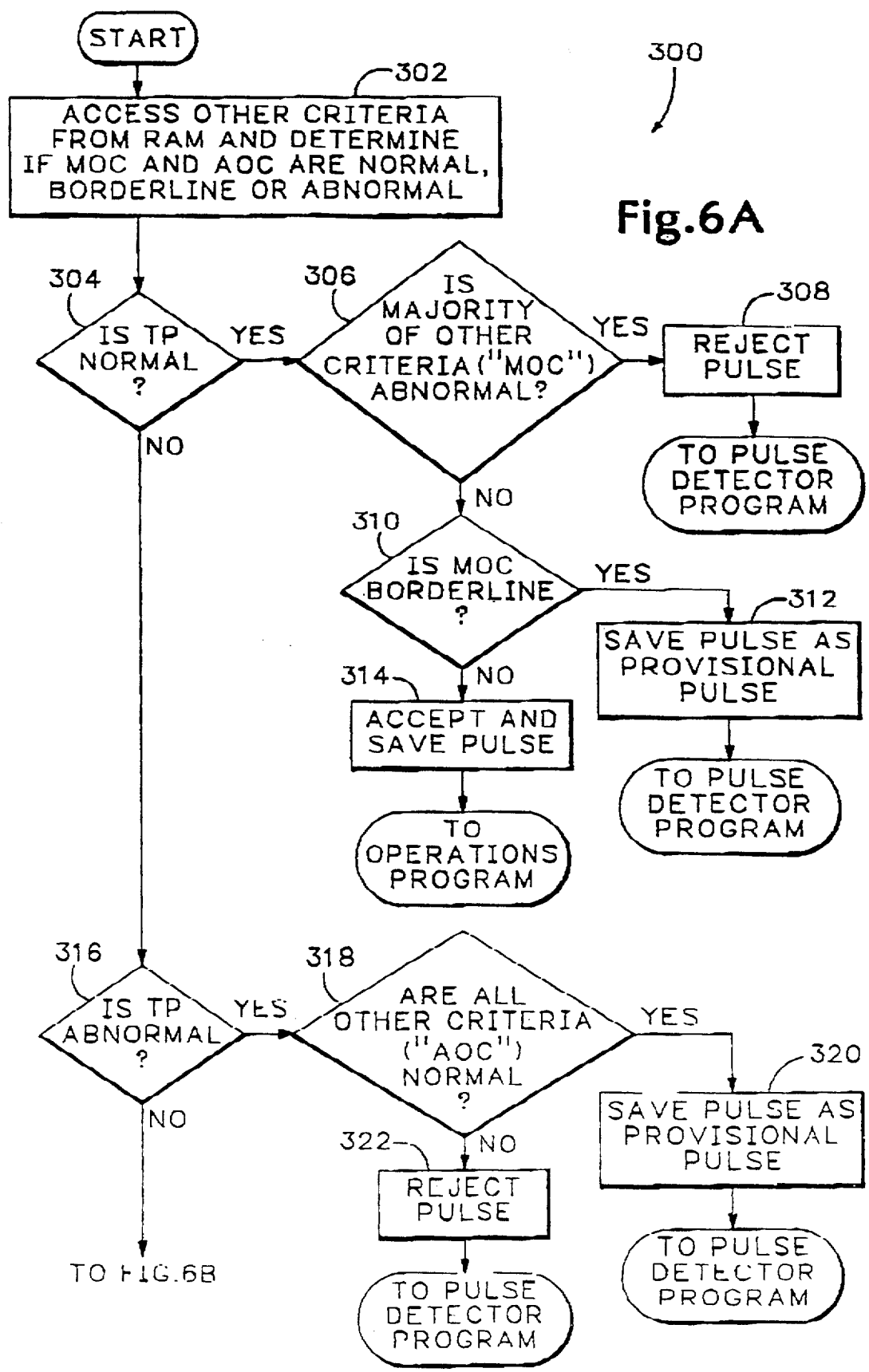

What is claimed is:

1. An improved method of validating whether pulse-like, physiologic events monitored by vital signs monitoring apparatus connected to a living subject are heartbeat-induced, with such apparatus being capable of monitoring successively, both the pulses of such events and event-validating R-wave information, and being capable of providing other event-validating criteria which criteria are independent of R-wave-related information, comprising:

monitoring the occurrence of an R-wave and the occurrence of a pulse of such an event;
providing at least one of such other criteria;
analyzing, along with such provided criteria, time relationships extant between the R-wave and the pulse, wherein the analyzing step includes analyzing such time relationships by the substeps of detecting selected points of the two occurrences, noting the time period between those selected points, preselecting timing standards, labeling the time period based upon the preselected timing standards, and using the label with such other criteria to validate the event;

validating such event based upon the analyzing;

choosing for additional validation a number of additional, successive pairs of R-waves and pulses;

repeating the monitoring, providing, detecting, noting, labeling, using and validating steps for the chosen number of additional, successive pairs;

based upon the repeating, adapting the preselected timing standards based upon the already analyzed time relationships; and using validated events to determine vital signs of the subject.

2. The method of claim 1, wherein the monitoring step involves monitoring the occurrence of an R-wave followed by the occurrence of a pulse of such an event.

3. The method of claim 2, wherein the monitoring step involves monitoring an oscillometric pulse as each pulse of such an event.

4. An improved method of validating whether pulse-like, physiologic events monitored by vital signs monitoring apparatus connected to a living subject are heartbeat-induced, with such apparatus being capable of monitoring both the pulses of such events and event-validating R-wave information, and being capable of providing other event-validating criteria which criteria are independent of R-wave-related information, comprising:

monitoring the occurrence of an R-wave and a pulse of such an event;

providing at least one of such other criteria;

analyzing, along with such provided criteria, time relationships extant between the R-wave and the pulse;

validating such event based upon the analyzing;

using validated events to determine vital signs of the subject; and with the analyzing of such time relationships including the substeps of detecting selected points of the two occurrences, noting the time period between those selected points, labeling the time period based upon preselected timing standards, and using the label with such other criteria to validate the event, and with the labeling substep including the substep of categorizing each time period, relatively and preliminarily, based upon whether each time period meets such timing standards, with such categorizing relating to the possibility of each event being validated in the validating step, and with the using substep including a wait-and-see (WAS) approach in accordance with Chart I above, toward the ultimate validation of such events based upon the analyzing.

5. An improved method of validating whether pulse-like, physiologic events monitored by vital signs monitoring apparatus connected to a living subject are heartbeat-induced, with such apparatus being capable of monitoring both the pulses of such events and event-validating R-wave information, and being capable of providing other event-validating criteria which criteria are independent of R-wave-related information, comprising:

monitoring the occurrence of an R-wave and the occurrence of a pulse of such an event;

providing at least one of such other criteria;

performing a first analyzing step by evaluating time relationships extant between the R-wave and the event;

performing a second analyzing step by evaluating the analyzed time relationships along with such provided criteria;

validating such event based upon the second analyzing step; and using validated events to determine vital signs of the subject.

6. The method of claim 5, wherein the step of performing the first analyzing step includes the substeps of detecting selected points of the two occurrences, noting the time period between those selected points, selecting timing standards, categorizing each time period, relatively and preliminarily, based upon the selected timing standards, and wherein the validating step includes the substeps of choosing standards corresponding to such provided criteria, categorizing preliminarily such provided criteria based upon the chosen standards, and using each categorized time period with such other categorized, provided criteria to validate the event.

* * * * *

UNITED STATES PATENT AND TRADEMARK OFFICE
CERTIFICATE OF CORRECTION

PATENT NO. : 5,339,822
DATED : August 23, 1994   Page 1 of 5
INVENTOR(S) : Lee A. Taylor et al It is certified that error appears in the above-indentified patent and that said Letters Patent is hereby corrected as shown below:

Figures 4-7 should be deleted to be replaced with figures 4-7 as shown on the attached sheets.

Signed and Sealed this

Twenty-first Day of March, 1995

Attest:

BRUCE LEHMAN

Attesting Officer   Commissioner of Patents and Trademarks